(12) United States Patent
Bagga et al.

(10) Patent No.: US 7,544,196 B2
(45) Date of Patent: Jun. 9, 2009

(54) SYSTEM AND KIT FOR DELIVERY OF RESTORATIVE MATERIALS

(75) Inventors: Charanpreet S. Bagga, Phoenixville, PA (US); Stephen G Gilbert, West Chester, PA (US); Antony Koblish, Malvern, PA (US); Maarten Persenaire, Phoenixville, PA (US); Erik M. Erbe, Berwyn, PA (US)

(73) Assignee: Orthovita, Inc., Malvern, PA (US)

( * ) Notice: Subject to any disclaimer, the term of this patent is extended or adjusted under 35 U.S.C. 154(b) by 494 days.

(21) Appl. No.: 10/654,543

(22) Filed: Sep. 2, 2003

(65) Prior Publication Data

US 2004/0092946 A1 May 13, 2004

Related U.S. Application Data

(63) Continuation-in-part of application No. 09/788,943, filed on Feb. 20, 2001, now Pat. No. 6,613,018.

(51) Int. Cl.
*A61B 17/58* (2006.01)
*A61B 17/60* (2006.01)

(52) U.S. Cl. ............................... 606/93; 606/92; 606/94

(58) Field of Classification Search ................ 606/80, 606/93, 92, 94, 185, 191, 192, 194, 184, 606/167, 170; 604/164.01, 164.06
See application file for complete search history.

(56) References Cited

U.S. PATENT DOCUMENTS

| | | | |
|---|---|---|---|
| 4,186,745 A * | 2/1980 | Lewis et al. ................ 604/265 |
| 4,230,123 A | 10/1980 | Hawkins, Jr. ............... 128/658 |
| 4,469,109 A | 9/1984 | Mehl ........................... 128/753 |
| 4,737,146 A | 4/1988 | Amaki et al. ................. 604/51 |
| 4,793,363 A | 12/1988 | Ausherman et al. ......... 128/754 |
| 4,838,282 A | 6/1989 | Strasser et al. .............. 128/754 |
| 4,994,033 A * | 2/1991 | Shockey et al. ........ 604/101.02 |
| 5,195,974 A | 3/1993 | Hardy ......................... 604/110 |
| 5,304,121 A | 4/1994 | Sahatjian ...................... 604/53 |
| 5,500,013 A * | 3/1996 | Buscemi et al. ............ 623/1.22 |
| 5,514,137 A | 5/1996 | Coutts ........................... 606/62 |
| 5,595,172 A | 1/1997 | Reese .......................... 128/200 |
| 5,601,559 A | 2/1997 | Melker et al. ................. 606/79 |
| 5,685,852 A | 11/1997 | Turkel et al. ................. 604/159 |
| 5,702,373 A | 12/1997 | Samson ....................... 604/282 |

(Continued)

FOREIGN PATENT DOCUMENTS

DE 31 15 763 A1 11/1982

(Continued)

OTHER PUBLICATIONS

Chiras, J., et al., "Percutaneous Vertebroplasty," *J. Neuroradiol.*, 1997, 24, 45-59 (Engish translation).

(Continued)

*Primary Examiner*—Pedro Philogene
(74) *Attorney, Agent, or Firm*—Woodcock Washburn, LLP (57) ABSTRACT

Novel kits are provided for the delivery of restorative or injectable compositions into an intraosseous space or surgical defect comprising cannulae for accessing an intraosseous space, mandarins insertable into the cannulae and movable therein, one or more catheters and a system for the delivery of aliquots of restorative compositions into the space via the catheters.

14 Claims, 11 Drawing Sheets

U.S. PATENT DOCUMENTS

| | | | |
|---|---|---|---|
| 5,795,332 A | 8/1998 | Lucas et al. | 604/96 |
| 6,019,765 A | 2/2000 | Thornhill et al. | 606/94 |
| 6,019,776 A | 2/2000 | Preissman et al. | 606/185 |
| 6,033,411 A | 3/2000 | Preissman | 606/99 |
| 6,048,343 A | 4/2000 | Mathis et al. | 606/72 |
| 6,048,346 A | 4/2000 | Reiley et al. | 606/92 |
| 6,127,597 A | 10/2000 | Beyar et al. | 606/86 |
| 6,140,452 A | 10/2000 | Felt et al. | 528/60 |
| 6,231,615 B1 | 5/2001 | Preissman et al. | 623/23.73 |
| 6,241,734 B1 * | 6/2001 | Scribner et al. | 606/93 |
| 6,248,110 B1 | 6/2001 | Reiley et al. | 606/93 |
| 6,273,916 B1 | 8/2001 | Murphy | 623/23.62 |
| 6,437,018 B1 * | 8/2002 | Gertzman et al. | 523/116 |
| 6,613,018 B2 | 9/2003 | Bagga et al. | 604/187 |
| 6,671,561 B1 * | 12/2003 | Moaddeb | 607/120 |
| 6,730,095 B2 | 5/2004 | Olson, Jr. et al. | 606/93 |
| 7,019,192 B2 * | 3/2006 | Gertzman et al. | 623/16.11 |
| 7,069,634 B1 * | 7/2006 | Elsberry | 29/447 |
| 7,081,122 B1 * | 7/2006 | Reiley et al. | 606/185 |
| 2001/0025157 A1 * | 9/2001 | Kriesell | 604/132 |
| 2002/0058947 A1 | 5/2002 | Hochschuler et al. | 606/94 |
| 2002/0120240 A1 | 8/2002 | Bagga et al. | 604/264 |

FOREIGN PATENT DOCUMENTS

| | | | |
|---|---|---|---|
| WO | WO 90/06150 | * 6/1990 | 606/80 |
| WO | WO 98/56301 A1 | 12/1998 | |
| WO | 99/02214 A1 | 1/1999 | |
| WO | 00/09024 A1 | 2/2000 | |
| WO | WO 02/07810 A2 | 1/2002 | |

OTHER PUBLICATIONS

Deramond, H., et al., "Percutaneous Vertebroplasty," *Seminars in Musculoskeletal Radiology*, 1997, 1(2), 283-295.

Gangi, A., et al., "Percutaneous vertebroplasty guided by a combination of CT and fluoroscopy," *AJNR*, Jan. 1994, 83-86.

Heini, P.F., et al., "Percutaneous transpedicular vertebroplasty with PMMA: operative technique and early results," *Eur. Spine J.*, 2000, 9, 445-450.

Jensen, M.E., et al., "Percutaneous polymethylmethacrylate vertebroplasty in the treatment of osteoporotic vertebral body compression fractures: technical aspects," *AJNR*, Nov. 1997, 18, 1897-1904.

* cited by examiner

SYSTEM AND KIT FOR DELIVERY OF RESTORATIVE MATERIALS

CROSS-REFERENCE TO RELATED APPLICATIONS

This application is a continuation-in-part of U.S. application Ser. No. 09/788,943, filed Feb. 20, 2001, now U.S. Pat. No. 6,613,018, incorporated herein by reference in its entirety.

FIELD OF THE INVENTION

This invention relates to kits for the delivery of restorative compositions into an intraosseous space, especially kits, usable in percutaneous surgical procedures, such as percutaneous vertebroplasty. This invention is also directed to systems for the delivery of aloquets of restorative compositions into a desired space especially via catheters. This invention is also directed to kits for creating a space within a vertebral body or intraosseous space, into which restorative composition may then be injected. The kits may comprise needles/cannulae, stylets/mandarins, syringes, and/or expandable reamers.

BACKGROUND OF THE INVENTION

Percutaneous surgical procedures have come to the forefront of the orthopaedic and neurological surgery fields, in an effort to limit exposure of tissues, reduce operating time, speed up recovery time and minimize patient scarring. Percutaneous vertebroplasty is a procedure by which, currently, acrylic cement, typically polymethylmethacrylate ("PMMA") or a material such as Cortoss® Synthetic Cortical Bone Void Filler (Orthovita, Inc., Malvern, Pa.), is injected into the vertebral body by a percutaneous route in order to prevent vertebral body collapse and pain in patients with unhealthy vertebral bodies. Percutaneous injection is minimally invasive compared to the alternative of exposing the entire soft and hard tissue at the surgical site. Percutaneous injection has also been indicated as a means of pain relief and restoration in patients with vertebral hemangiomas, painful vertebral body tumors, as well as painful osteoporosis with loss of height and/or compression fractures of the vertebral body. See, e.g., Gangi, A., et al. Percutaneous Vertebroplasty Guided by a Combination of CT and Fluoroscopy, AJNR 15:83-86, January 1994 ("Gangi"). All references cited in this specification are incorporated herein by reference.

U.S. Pat. Nos. 6,033,411 and 6,019,776 to Preissman, et al. disclose methods for controlled approach to the interior of a vertebral body by inserting a threaded or sharp-pointed mandarin and cannula percutaneously through the soft tissue of an organism until abutting the soft tissue; further inserting the mandarin into a predetermined location within the hard tissue; ratcheting a pawl mechanism or rotating a camming mechanism to advance the cannula along the mandarin to the predetermined location; withdrawing the mandarin from the cannula and attaching a source of implantable material for injection of the material into the organism through the cannula.

U.S. Pat. No. 4,838,282 to Strasser, et al. ("Stasser") discloses a bone biopsy needle assembly for withdrawing samples of bone, bone marrow and other such fluids, which includes a cannula and stylet. The handles of the cannula and stylet are provided with features for mating reception when assembled together. In addition, both the cannula and stylet handles are comprised of two equal generally rectangular halves extending in diametrically opposed directions from the cannula axis.

U.S. Pat. No. 4,793,363 to Ausherman, et al. ("Ausherman") discloses a bone marrow biopsy device that includes a cannula member and a stylet member with a Luer-lock connector and handle locking arrangement.

U.S. Pat. No. 4,469,109 to Mehl ("Mehl") discloses a bone marrow aspiration needle including a cannula, with a cannula housing which supports the cannula, and a partially threaded lower member, and a stylet, with a stylet cap which supports the stylet and a threaded depth stop for engaging over the cannula.

U.S. Pat. No. 5,601,559 to Melker, et al. ("Melker") discloses an intraosseous needle having a threaded shaft with two side ports, which allow fluids to pass through the needle, and a tip having a plurality of cutting edges.

Heini, P. F. et al., Percutaneous Transpedicular Vertebroplasty with PMMA: Operative Technique and Early Results: A Prospective Study for the Treatment of Osteoporotic Compression Fractures, Eur. Spine J. (2000) 9:445-450 ("Heini"), discusses the use of various components for performing percutaneous transpedicular vertebroplasty including a 2.0 mm K-wire for accessing the center of the vertebral body and a bone marrow biopsy needle placed over the K-wire (which is subsequently removed) for positioning the needle. Heini also discloses the use of 2-cc standard syringes for injecting the material through the needle.

Gangi describes the percutaneous injection of PMMA into the vertebral body with the aid of CT and/or fluoroscopic guidance using a needle and 2-ml Luer-lock syringe mounted on a pressure regulator to facilitate the injection of the material.

Chiras, J., et al., Percutaneous Vertebroplasty, J Neuroradiol, 1997, 24, 45-59 ("Chiras") discloses cannulae of 10 to 15 cm in length with a beveled edge lumen and diameter of 3 mm as being standard equipment for vertebroplasty.

Deramond, H., et al., Percutaneous Vertebroplasty, Seminars In Musculoskeletal Radiology, Vol.1, No.2, 1997: 285-295 ("Deramond"), discloses the use of various materials for percutaneous vertebroplasty ("PVP") including ten-gauge needles, 10 to 15 cm long, with a beveled extremity, fifteen-gauge needles, 5 to 7 cm long, with a tapered tip, Luer-lock syringes of 2 or 3 cc, a syringe handle and bone cement. Deramond suggests that leakage can be avoided by making injections under lateral fluoroscopic control or inserting the cannula into the lateral part of the vertebral body.

Jensen, M. E., et al., Percutaneous Polymethylmethacrylate Vertebroplasty in the Treatment of Osteoporotic Vertebral Body Compression Fractures: Technical Aspects, AJNR 18:1897-1904, November 1997 ("Jensen") discusses the use of various components for performing vertebroplasty procedures including a disposable 11-gauge Jamshidi needle and stylet for accessing a desired space, and both 10-ml and 1-ml syringes and an 18-gauge needle for the injection of material through the needle. Jensen, et al. teaches that the material should be allowed to set only if a leak should occur.

In the art, if a leak is detected, the operator either stops the procedure altogether, continues with the injection of more material using a different "batch" of material, or allows the material that already has been injected to thicken. Clinically, using a different "batch" of material requires the surgeon to open another "batch" of material, which is costly and not desirable or practical in the case of standard restorative materials such as PMMA. Often in the case of a leak, the surgeon does not allow the material to set, but rather waits until the material reaches a pasty stage (thicken) prior to injecting more material. This approach, however, prevents the surgeon from injecting the desired amount of material, since once the material becomes pasty, he has little time to work and must forcefully inject additional material prior to the material setting in the cannula. If the material hardens in the cannula, the cannula will have to be removed and reinserted for additional doses. Surgeons are very skeptical about doing this because of the extreme difficulty in reinserting another cannula in the same exact place as the one removed.

Even before the introduction of restorative material, an operator may be interested in clearing out an existing portion of cancellous bone, thereby creating a space that is ready for the procedures described above. The creation of a space in a vertebral body during vertebral augmentation for the treatment of vertebral compression fractures (VCF's) has generated significant interest as illustrated by the prolific use of kyphoplasty instrumentation. But this technique is imperfect in that the significant pressures that are generated within the kyphoplasty balloon can displace fat emboli into the venous blood stream, a phenomenon that could lead to pulmonary emboli. It would be advantageous to create a similar cavity while minimizing the pressure generation and displacement of fat emboli. Another problem with inflatable balloons is that during inflation they follow the path of least resistance, such that if there is a crack in the bone or vertebral body endplate, the balloon will herniate out through the crack, thereby preventing further compression of the cancellous bone. A solid compression device may eliminate this problem, as its shape will stay within the bony volume.

It is an object of this invention to provide kits for minimally invasive delivery of restorative composition into an intraosseous space.

It is a further object of this invention to provide a solid compression device for creating or enlarging a cavity in a vertebral body or intraosseous space.

Additional objects, advantages and novel features of this invention will become apparent to those skilled in the art upon examination of the following descriptions, figures and claims thereof, which are not intended to be limiting.

SUMMARY OF THE INVENTION

This invention relates to device combinations and packaged kits for the delivery of a restorative or injectable composition into an intraosseous space. These comprise one or more cannulae adapted for accessing said intraosseous space; one or more stylets/mandarins insertable into the hollow cavity of the cannula and being movable therein to advance the cannula into position. These are adapted for accessing said intraosseous space. The kits and systems preferably also have one or more catheters that are insertable into the cannulae, stylets that are sized to fit within the catheters to advance material therethrough; and a system for delivery of aliquots of said restorative or injectable composition into the intraosseous space via the catheters. The kits can also include a micro-reamer that fits within the hollow cavity of the cannula (after removal of the stylet and before insertion of the catheter) to make a channel for material delivery via the catheter. Fixed to the proximate end of each of the cannulae, stylet, and micro-reamer is a substantially lateral surface (flat, solid knob or pedestal) responsive to impact blows. The cannula, micro-reamer and catheter may also include gradations. The catheter may also comprise a single distal aperture, or a plurality of apertures along some portion of its distal region. The kit may also include a device for the creation or enlargement of a cavity in a vertebral body or any metaphyseal bone area; a description of one embodiment of such a device appears below.

Some catheters of the present invention may have a distal end and at least one placement orifice disposed proximate to the distal end, wherein the placement orifice may be adapted for dispensing the restorative or injectable composition directly from the distal end or radially therefrom. Such adaptation may include partially covering the distal end with high-porosity material to achieve multi-directional diffusion of the restorative or injectable material. Catheters used in the kits may comprise stainless steel, polyimide, latex, silicone, vinyl, or other polymer suitable in the art. They may be flexible for maneuverability and be long and of such material that they can be cut to size at the time of use.

The kits can preferably further comprise a plurality of syringes having an aperture on a distal end providing fluidic passage therethrough from a bore being engageable within said aperture; as well as a locking mechanism, such as a Luer-lock type of locking mechanism, for engaging a proximal end of the catheter for dispensing of the material into the space through the catheter. In a preferred embodiment, the kit includes a plurality of syringes including a 1 cc, 3 cc and 5 cc syringes.

This invention also relates to a system for the delivery of a restorative or injectable composition to specific intraosseous space wherein the placement of aliquots of said restorative or injectable composition is under tactile feedback control of a human operator, such as a surgeon or interventionalist. The restorative or injectable composition can comprise a hydrogel, synthetic bone void filler, polymethylmethacrylate, or replicated bone marrow.

The present invention also relates to kits for the delivery of restorative or injectable compositions comprising at least one cannula; at least one stylet; at least one catheter comprising a high-porosity tip; and a system for delivery of aliquots of the restorative or injectable composition into the intraosseous space via said catheter. The high-porosity tips may comprise polylactic acid and may be biocompatible, bioresorbable and/or bioactive. The tips may be partially coated with non-porous or semi-porous material.

Additionally, the kits of the present invention may comprise an expandable micro-reamer for creating or enlarging a cavity in a vertebral body or intraosseous space. This micro-reamer may comprise an expandable cylindrical section that may be placed through a cannula or tube that is positioned within the vertebral body or intraosseous space. The expandable cylindrical section is in communication with the outer shaft and surrounds an inner shaft. The cylindrical section may be moved to effect tamping or cutting. In one embodiment, the cylindrical section, once compressed, expands to create an ovoid shape. The size of the ovoid shape created is dependent upon the aspect ratio and volume of the expandable cylindrical section. As, defined herein, the aspect ratio is the ratio of the expanded height divided by the expanded width. The kits of the present invention may include multiple micro-reamers that expand to create various defect sizes.

In another embodiment, the micro-reamer is rotated to effect cutting. The expandable section may comprise an elastic metal, a composite metal, a polymer, or suitable material known in the art that is able to expand and regain its original form. One embodiment of the expandable section may comprise nitinol.

The location of the expandable cylindrical section along the length of the micro-reamer may vary; alternatively, the length of the micro-reamer itself may vary to provide the user with a device that can be placed in bones and defects of all sizes.

This invention also relates to device combinations and packaged kits for both the creation and/or enlargement of a space in a vertebral body or intraosseous space and for the delivery of a restorative or injectable composition into such spaces. Such kits may comprise an expandable micro-reamer or bone tamp, one or more cannulae adapted for accessing said intraosseous space, one or more stylets/mandarins insertable into the hollow cavity of the cannula and being movable therein, at least one catheter that is insertable into the cannulae, and a system for delivery of aliquots of the restorative or injectable composition into the intraosseous space via said catheter.

PREFERRED EMBODIMENTS

Figure 1:
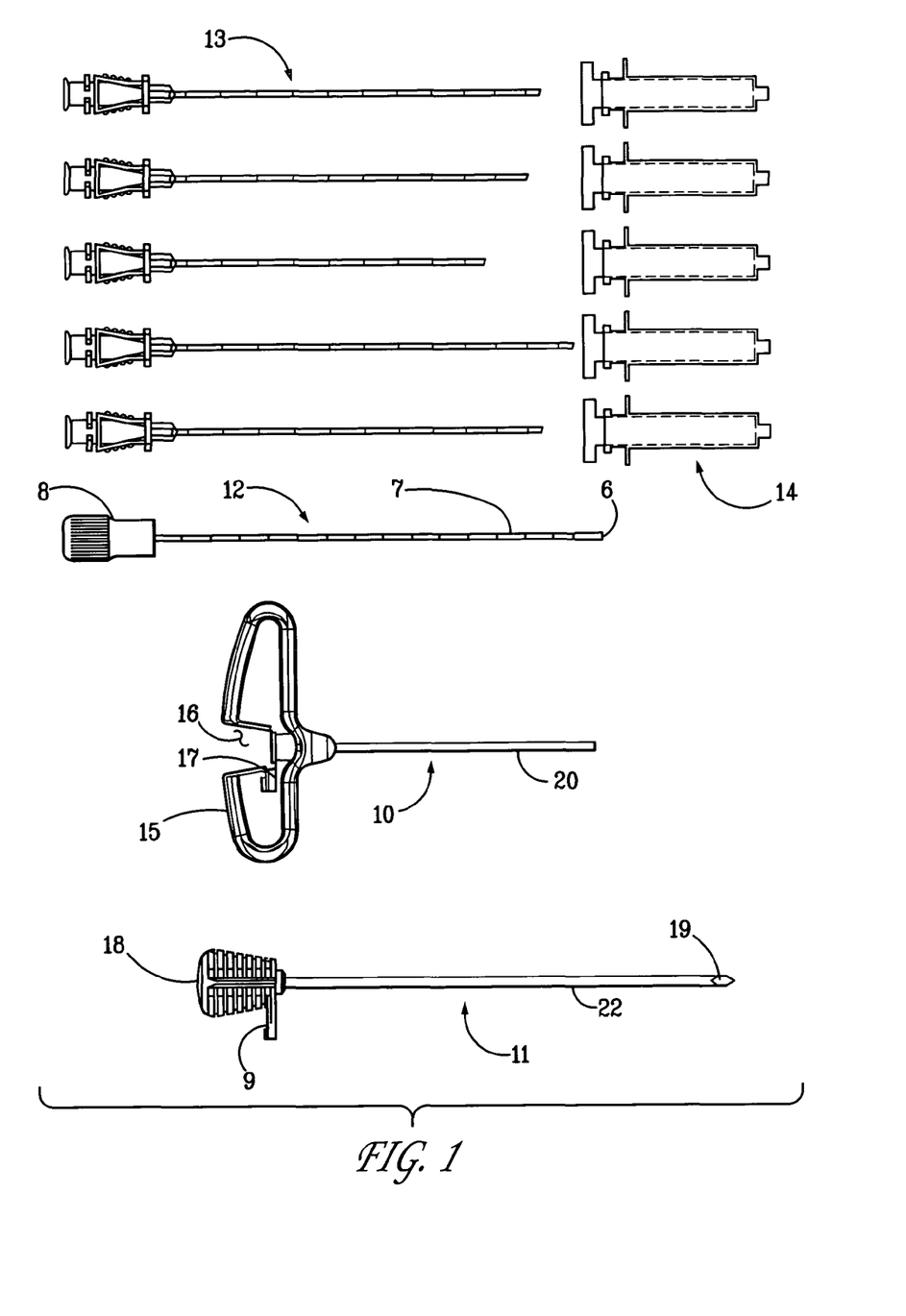
FIG. 1 depicts a kit of an embodiment of the present invention showing a cannula and stylet, a micro-reamer, and a plurality of catheters and syringes.

The present invention provides kits for the delivery of a restorative or injectable composition. Typically, the kits, such as the kit shown, for example, in FIG. 1, comprise at least a cannula 10 or needle. More typically, the cannula is adapted for accessing particular intraosseous spaces. In accordance with one embodiment, the cannula 10 is an 5 to 14 gauge, or preferably an 11 to 12-gauge needle having a solid handle 15 for absorbing impact and force upon insertion into bone, and a hollow bore 20 component attached thereto. The handle 15 is asymmetrically shaped to accommodate a user's hand and includes a space 16 for receiving the unidirectional stylet/mandarin 11 (or other instruments).

Figure 3:
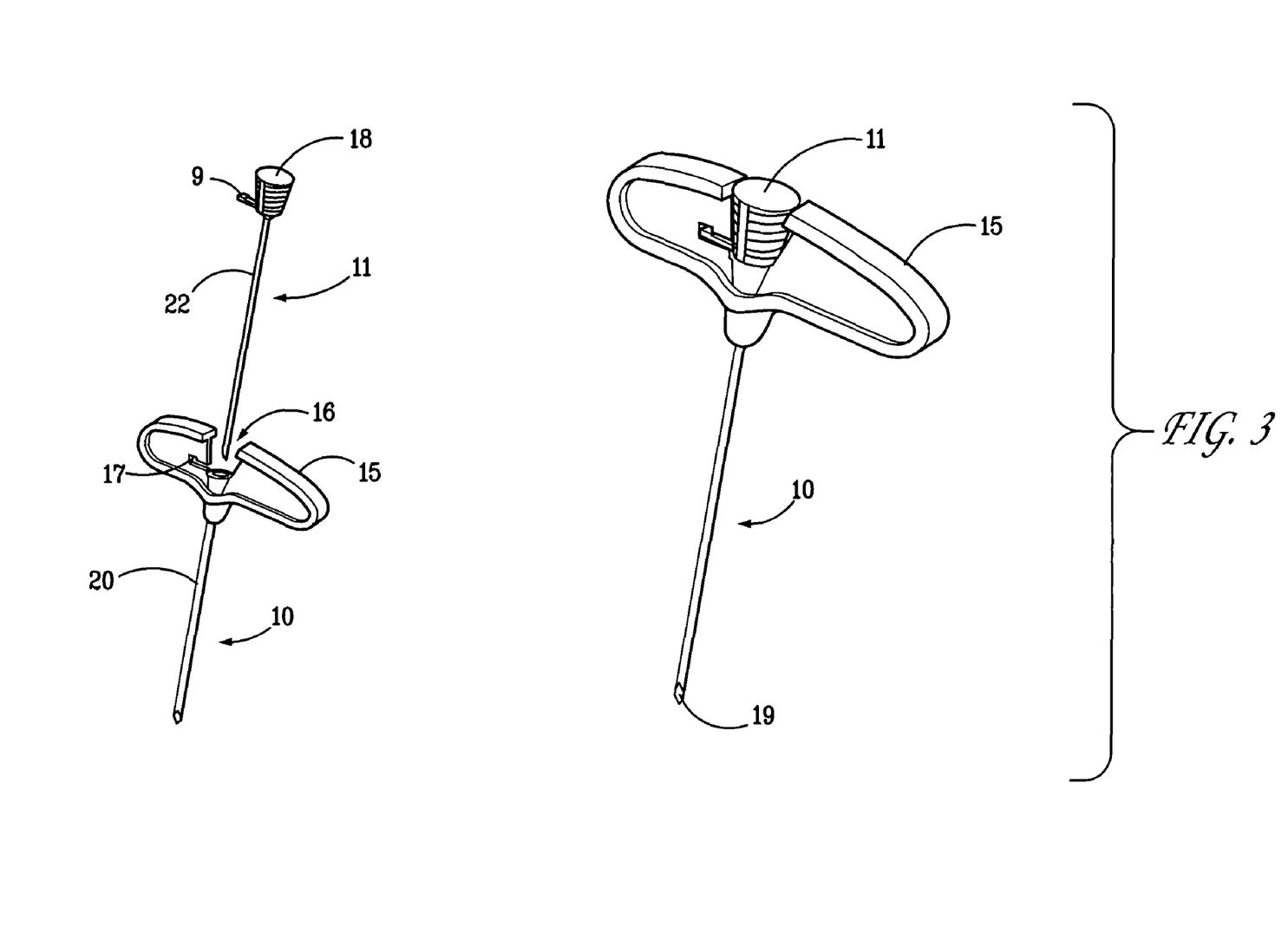
FIG. 3 depicts a cannula/stylet locking mechanism.
Figure 4:
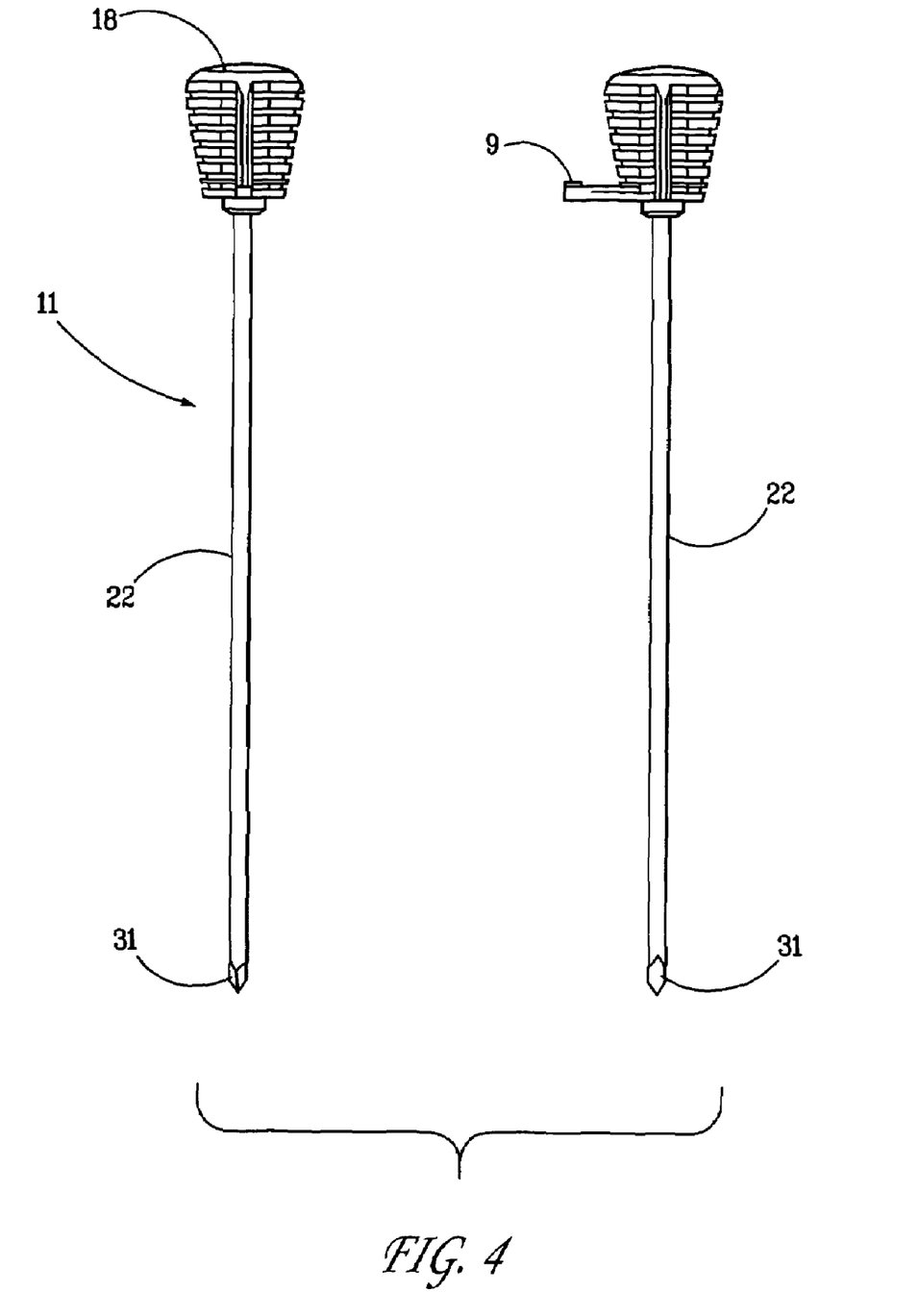
FIG. 4 depicts an alternative embodiment stylet tip.

One or more stylets 11 adapted for accessing an intraosseous space are preferred in some embodiments. Typically, the stylet 11 comprises a solid, impactable knob or head 18, which is tapered for easy insertion and removal into the receiving space 16 of the handle 15 of the cannula 10, and an elongated solid stem 22 with a beveled tip 19 (for steering capabilities) or diamond tip 31 that sits within the bore 20 of the cannula 10 when in use (see, for example, FIG. 4). The unidirectional fit allows for a pin 9 within the knob 18 of the stylet 11 to lock within a corresponding recess 17 on the handle 15 of the cannula 10 (see, for example, FIG. 3). Specifically, mating occurs when the pin 9 of the stylet 11 is simultaneously displaced in the superior/inferior direction and rotated into the recess 17 of the cannula handle 15. This fit ensures that the stylet is always positioned correctly, thus creating a solid sharp beveled tip 19 or diamond tip 31. The cannula 10 and stylet 11 are used to gain access into the body cavity. Force from either screwing or tapping is used to propel both the cannula 10 and stylet 111 into the osseous space.

Once the space is accessed by the cannula 10 and stylet 11, in some preferred embodiments, the stylet 11 is removed and a micro-reamer 12 is inserted to create room or an opening in the bone for placement of the restorative or injectable composition. The micro-reamer 12 conveniently has a knob 8 similar to that of the stylet knob 18 but without a pin being engageable within the cap of the needle. The absence of the pin allows the operator to insert and rotate the micro-reamer 12 about the space. In many forms of this invention, the micro-reamer 12 is used to create a channel, which facilitates the insertion of the catheter (and subsequently, material delivery). The rotation of the micro-reamer 12 creates some debris that helps block the venous pathways, and thus reduce the potential for leakage. In other forms of this invention, the micro-reamer 12 is fitted with a cutting means 6.

The shaft 7 of the micro-reamer 12 is generally longer than the shaft 20 of the cannula. It can extend from about 1.0 cm to 3.0 cm (and all combinations and subcombinations of ranges and specific volumes therein) out of the distal tip of the cannula 10 when fully inserted. Typically, the length of the second shaft of the catheter is about equal in length to the length of the micro-reamer 12 when fully inserted into the cannula. Micro-reamers of varying lengths can be used depending on the approach an operator uses to access an intraosseous space. In certain embodiments, when accessing a vertebral space, the tip of the cannula 10 remains in the inner opening of the bone while the elongated micro-reamer 12 accesses the opposite cortex of the vertebral space. In other embodiments, the micro-reamer is shaped, bent, or made from a shape memory material, which allows extra bending, so as to create a wider channel space for the catheter.

Figure 2:
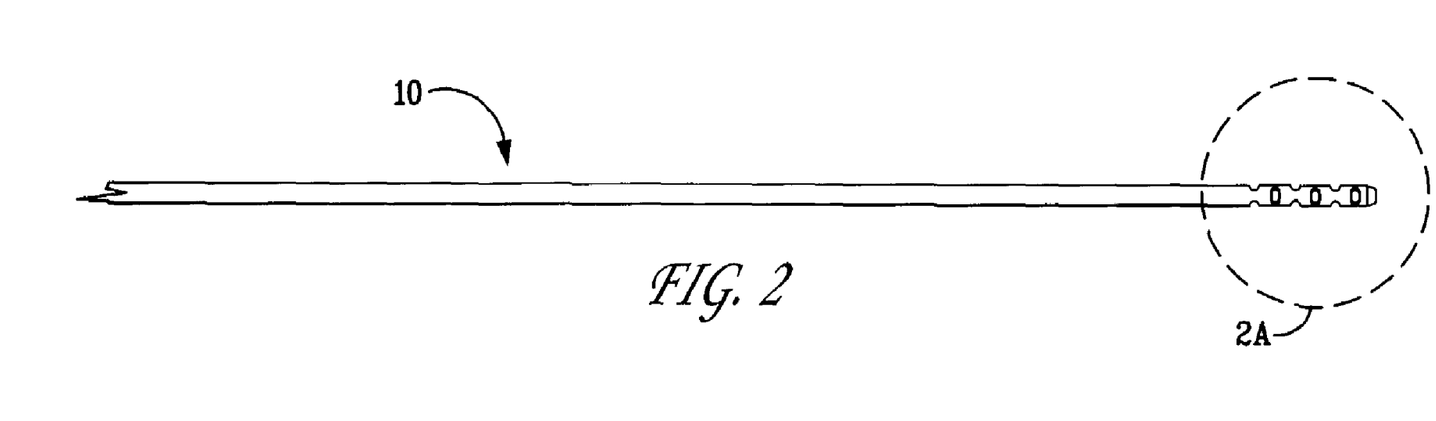
FIG. 2 depicts an embodiment of the present invention with a specialized distal end, with a plurality of apertures.
Figure 2A:
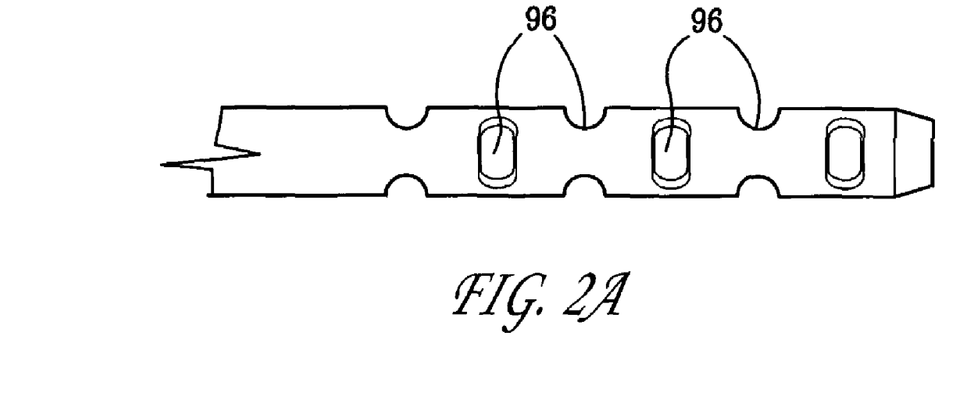

Once the micro-reamer 12 creates a space for the material, it is removed from the cannula 10 and replaced with a catheter 13. Catheters are used to deliver the restorative or injectable composition into the intraosseous space. Another embodiment of the catheter may comprise a plurality of apertures 96 (see FIG. 2) to achieve radial or multi-directional dispersal of a restorative composition. Multi-directional dispersal permits the human operator to achieve uniform release of a restorative material. FIG. 2 depicts a catheter 13 with a plurality of apertures 96, which may allow multi-directional distribution of restorative or injectable material into an intraosseous space. The quantity of apertures 96 may vary to accommodate assorted types of restorative or injectable materials or different procedures for their delivery, for example, to affect a particular rate of injection. The apertures 96 may be of uniform or varying shapes and sizes, and may be evenly or irregularly placed along the catheter 13. For instance, the apertures at the distal tip of the catheter may be smaller than those more proximal (or vice versa) to guide the flow of material in such a way as to prevent leakage of material out of the bony site. A preferred embodiment may comprise a set of elliptical apertures, uniformly arranged along some portion of the length of the catheter 13 (see FIG. 2, detail A).

Figure 10:
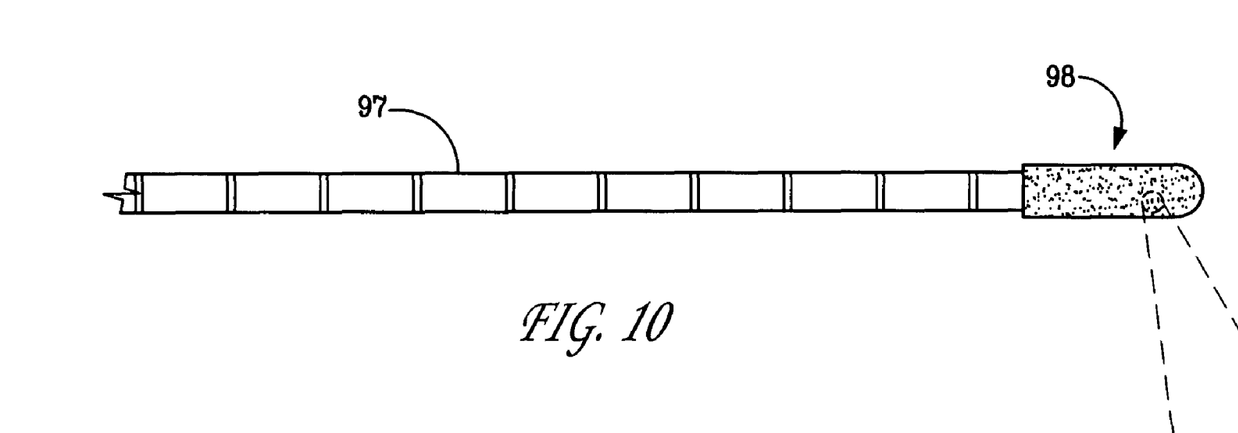
FIG. 10 depicts a catheter fitted with a high-porosity diffuser tip.
Figure 10A:
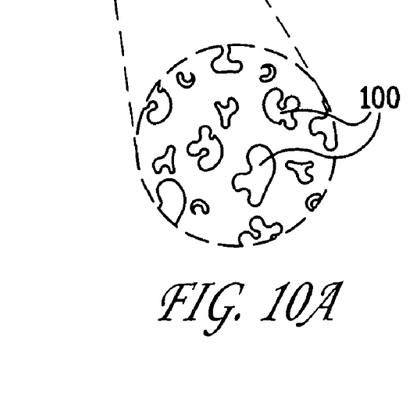

In one specific embodiment of this invention, a front-opening catheter 43 (see FIG. 5) is provided for delivery, and in another embodiment, a side-opening catheter 50 (see FIG. 6) is provided for radial delivery of the composition within an osseous space. The front-opening allows direct injection of the material into the site through the opening in the distal tip. The side-opening catheter 50 is useful for radial delivery of the composition within an osseous space since it allows for 360° directional control of the delivery of the restorative or injectable materials. In a further embodiment, the distal end of the catheter may have a high-porosity tip 98 (see FIG. 10), or directional diffuser. The diffuser-tipped catheter may fit through the cannula. As used herein, "high-porosity" means having a porosity that ranges from 60% to 99%. The composition flows through a plurality of pores 100 of the directional diffuser 98 as the operator applies injection pressure. The directional diffuser 98 permits uniform, multi-directional delivery of a restorative or injectable material. The directional diffuser 98 catheter may also contribute to the operator's ability to ensure that the proper quantity of the restorative or injectable composition is injected into the selected intraosseous space. The risk of introduction of excess material into the intraosseous space and surrounding areas is thereby reduced. The directional diffuser 98 may preferably comprise open-cell polylactic acid (OPLA®)a synthetic polymer scaffold that is synthesized from D,D-L,L polylactic acid, but may be any suitable high-porosity matter. As polylactic acid is biocompatible and resorbable, a diffuser tip comprising this material may be left in or near the intraosseous space following injection of the restorative or injectable composition. As used herein, biocompatible means that the material does not invoke an inflammatory response when contacted with mammalian bodily fluids and tissues. Alternatively, the diffuser tip 98 may be removed along with the catheter following injection. The diffuser may be partially coated with semi-porous or non-porous material 102 to control the direction of flow. The semi-porous or non-porous material may comprise a low porosity polymer-ceramic composite such as a PLLA/β-tricalcium phosphate composite or may include a biocompatible polymer, ceramic or metal such as titanium. The semi-porous or non-porous material may also be biocompatible or resorbable.

In typical embodiments, the catheters also include gradations or gradients 40 along the shaft to further aid in the delivery of the composition. These gradients 40 aid in the determination of the volume of restorative or injectable composition being injected and also the depth of the catheter within the space. Typically, the gradients 40 are placed at varying lengths suitable for each procedure and can be internal markings or external protrusions. More typically, these gradients 40 are made 1 cm apart and are external markings. The catheters of the present invention can be of varying volumes and lengths. It is appreciated that the distance the micro-reamer 12 extends out of the distal tip of the cannula 10 will vary depending on the nature of the space being accessed.

Figure 9:
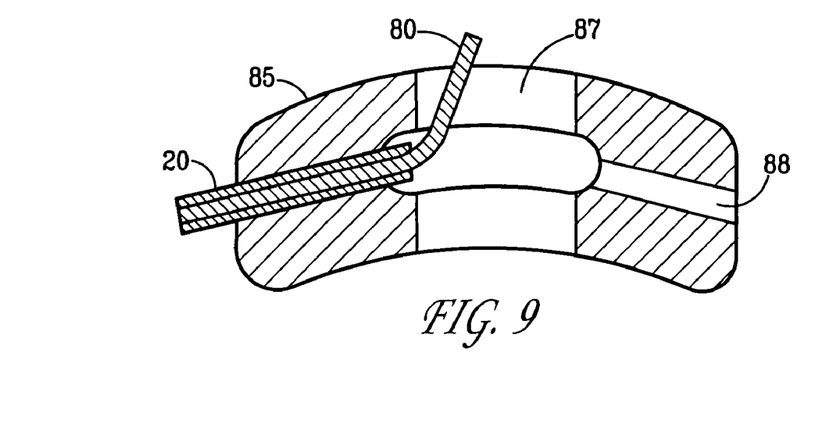
FIG. 9 depicts a shape memory embodiment of the catheter/micro-reamer.

Generally, the catheters are comprised of metals, such as stainless steel or titanium, which are rigid and readily visible by X-Ray; but may also be comprised of a plastic or polyimide, which can serve as a flexible element; latex; silicone; vinyl; or polymers other than those listed herein; or of a ceramic material. In other embodiments of the invention, the catheters are comprised of nitinol, or any other "shape memory" alloy. In this manner, the shape memory catheter 80 (or shape memory micro-reamer) could be placed through the cannula 20 into a structure, either an implant structure 85 or anatomical structure, with known openings 87, 88, which the shape memory catheter traverses for precise, directional delivery of material (see, for example, FIG. 9). In still more embodiments, the catheter is flexible for maneuverability and of such material that it can be cut to size at the time of use.

Figure 5:
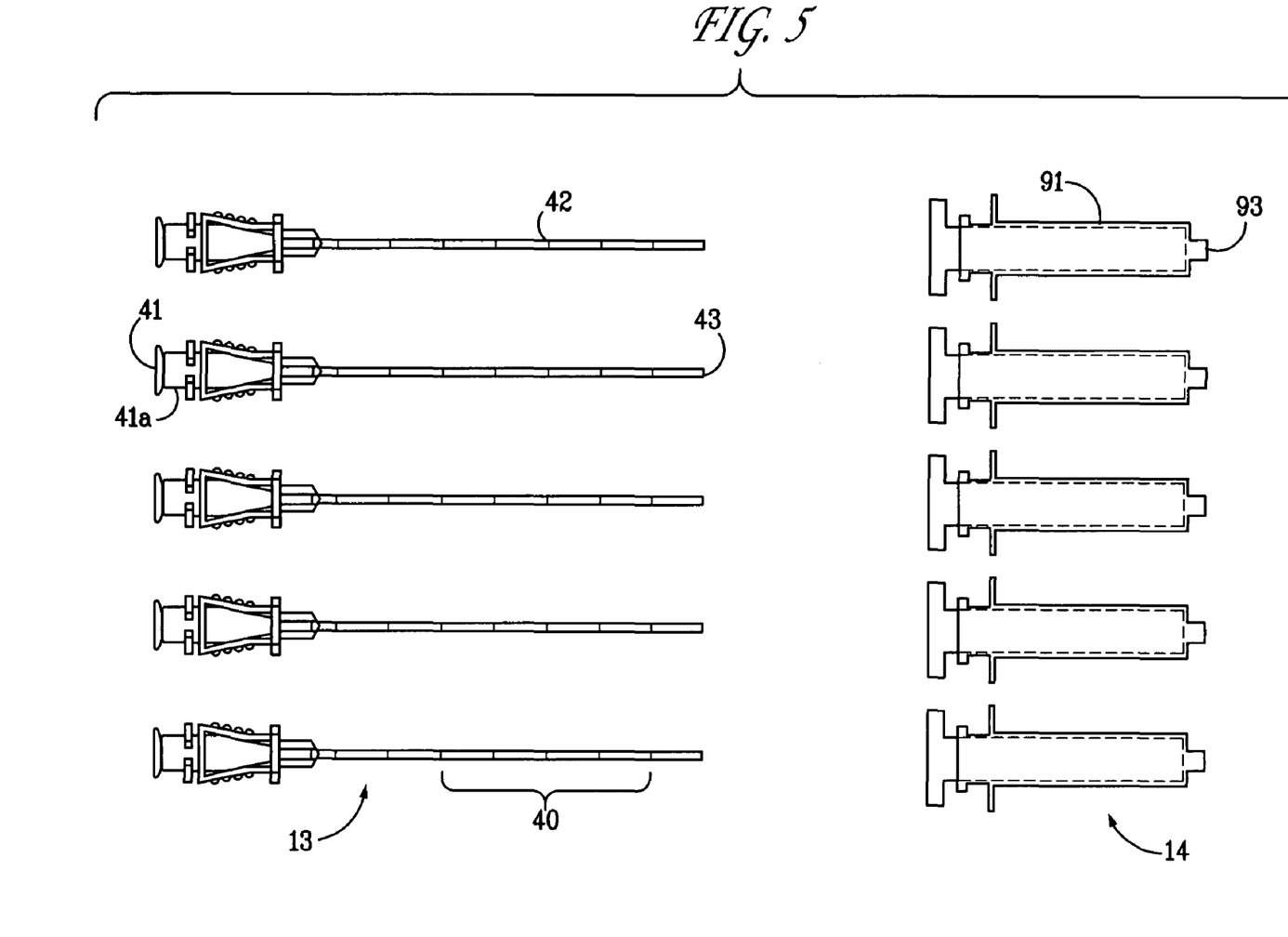
FIG. 5 depicts a kit of the present invention showing a plurality of catheters and syringes.
Figure 6:
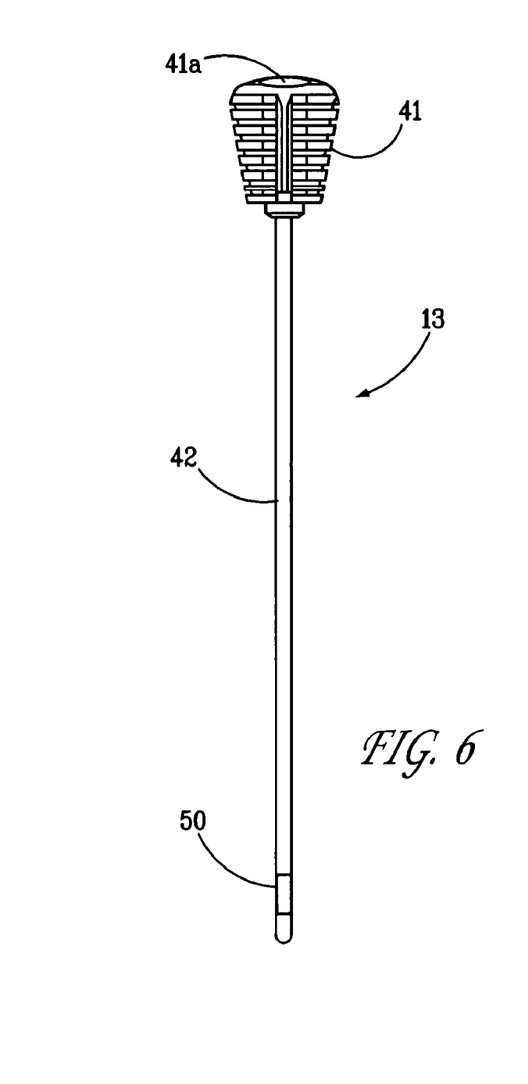
FIG. 6 depicts the side-opening feature of certain preferred catheters of the present invention.

In accordance with a specific embodiment of this invention, the catheter 13 has a knob 41 which has an adapter 41a for connecting to a syringe tip, such as a Luer-lock and a hollow shaft 42 extending therefrom (see FIG. 5). In some preferable embodiments, the catheter can be long (to distance the surgeon or user from any source of radiation that may be used during the surgical process). In other embodiments the catheter has two consecutive shafts with one having a plunger mechanism and the second shaft being engageable to the distal end of the first shaft by means of a Luer lock or other locking means better equipped to ensure non-leakage of the restorative or injectable composition.

Figure 7:
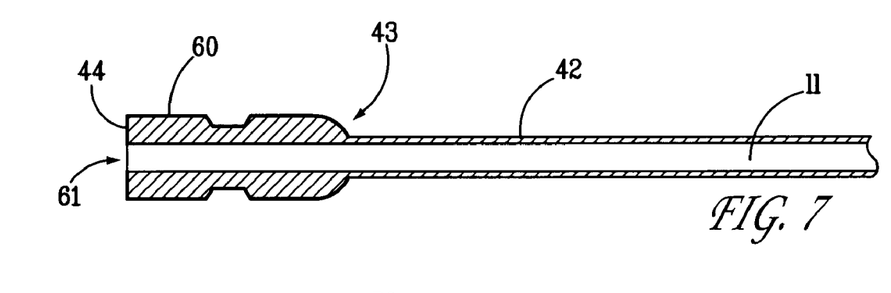
FIG. 7 depicts a front-opening catheter/cannula having a micro-reamer feature.
Figure 8:
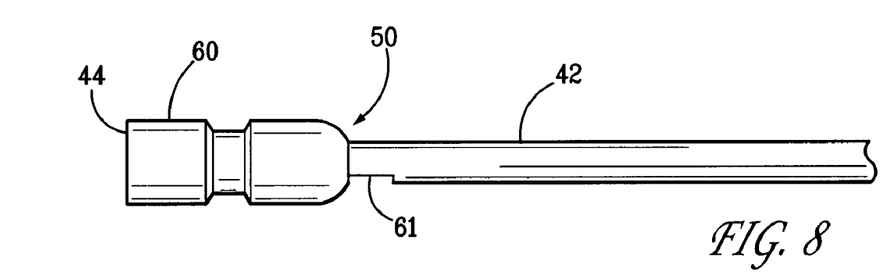
FIG. 8 depicts a side-opening catheter having a micro-reamer feature.

In one specific embodiment, such as the embodiment depicted in FIG. 7, the catheter is provided with protrusions or cutting elements on its distal end 44. In this manner, the catheter acts both as a micro-reamer and catheter. This feature can be added to both the front-opening catheter 43 (see FIG. 7) and side-opening catheter 50 (see FIG. 8) embodiments. More specifically, when added to the side-opening catheter 50, the cutting means 60 is attached to the distal end 44 so that the opening 61 (upon removal of the stylet 11) is more proximal to the handle than the cutting means 60. When added to the front-opening catheter 43, the cutting means 60 is more proximal to the handle than the opening 61. While in use, the stylet 11 is kept in place during the micro-reaming aspect of the procedure, and then removed for the injection of the material. The cannula of the present invention could also be provided with means for cutting in the same manner as the front opening catheter.

By providing kits with a catheter, the present invention overcomes the situation in which a procedure is halted due to leakage, the material hardens in the cannula and the cannula must be removed and replaced, or the situation in which the material thickens and becomes difficult to inject. In many embodiments, the kits of the present invention are provided with a plurality of catheters, which fit through the cannula. Once the material hardens, the first catheter is simply removed with the cannula in place and a new catheter is slipped in place for the next dose. Typically, the cannula never has to be removed and the operator does not run the risk of trying to reinsert the cannula in the same exact place.

Figure 11:
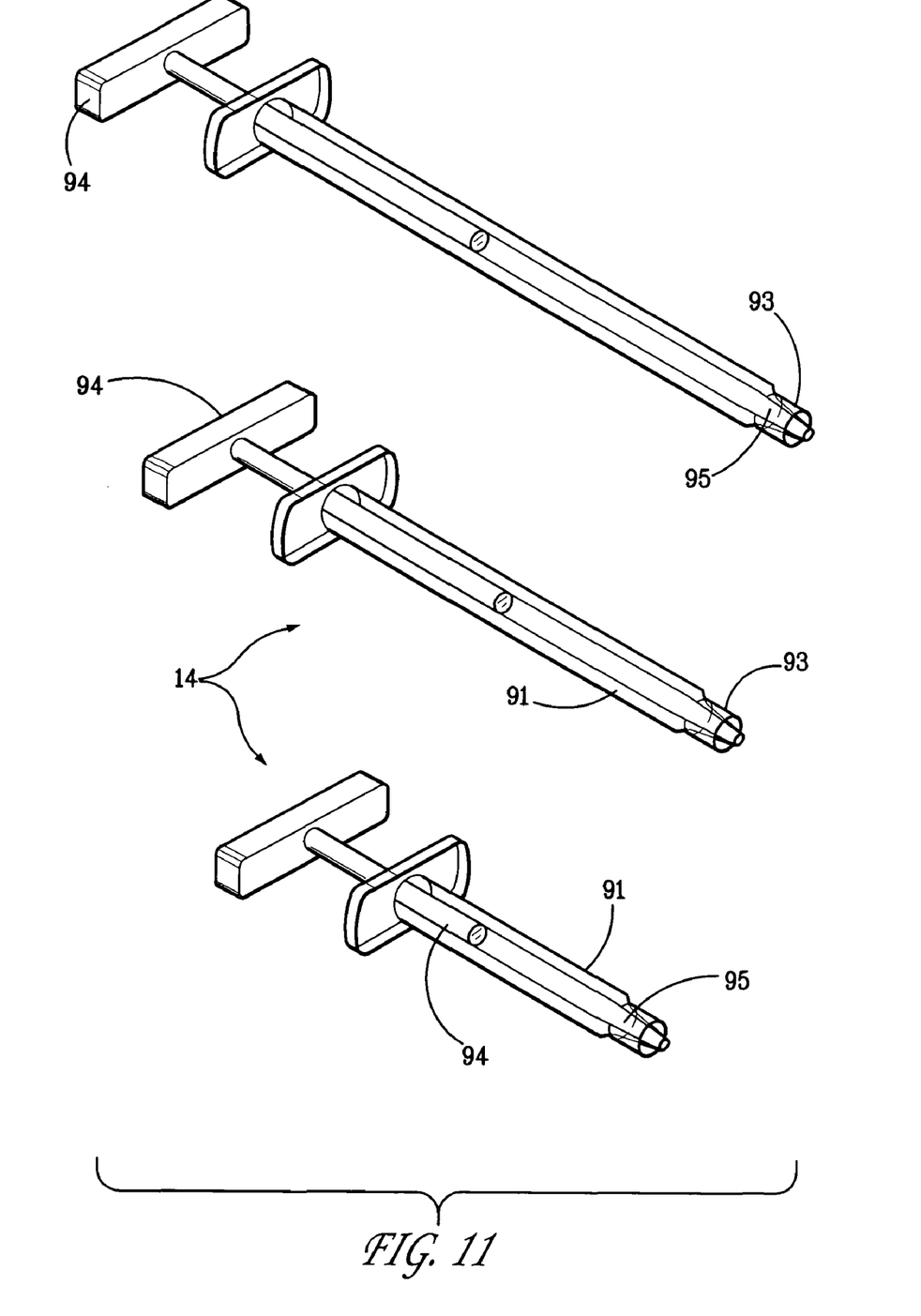
FIG. 11 depicts certain preferred syringes of the present invention kit.

In one embodiment such as the embodiment shown in FIG. 11, a syringe 14 attaches to the catheter for delivery of the material. Typically, a number of syringes are provided with the kits of the present invention, including standard, for example, 1 cc, 3 cc and 5 cc syringes. More typically, the syringes have an aperture 93 on one end for providing fluidic passage therethrough from a bore 95 being engageable within said aperture 93, and a plunger 94 that sits within the barrel 91 of the syringe 14. Material to be injected (not shown) is placed in the barrel 91 of the syringe 14 and then the plunger 94 is placed within the barrel 91 for material extrusion. The aperture 93 can be a Luer-lock type mechanism for engaging the proximal end of a catheter for injecting the restorative or injectable material into the space. In a preferred embodiment of the present invention, the 1 cc, 3 cc and 5 cc syringes are specially designed such that the diameters of the respective plungers 94 and the internal diameters of the respective barrels 91 are reduced, but are both the same size for each of the syringe sizes-1 cc, 3 cc and 5 cc syringes. Since the internal diameters of the barrels 91 of each of the different size syringes is the same, the volume differences between the syringes are compensated for by increasing the length of the syringe 14 barrel with increasing syringe size.

The amount of force required to inject material through the present invention syringes is generally reduced in each individual syringe since the cross-sectional area is reduced and the barrel 91 internal diameter and bore 95 diameter are closely matched. To further reduce the force required to move the material through the syringe, in a preferred embodiment, there is a gradual decrease in barrel 91 (internal) diameter at the tip of the syringe toward the bore 95. This gradual decrease better streamlines the material flow through the bore.

These syringes differ than those in the prior art in that the plunger/barrel internal diameters (and therefore, cross-sectional areas) of the prior art increase with increasing syringe size. Since the bore diameter does not change with increasing syringe size, increasing force (due to increased resistance) is required to inject the material through the bore as the syringe size/volume increases. When larger syringes (5 cc) are used to inject viscous materials that tend to thicken with time (in order to set), it is not uncommon for syringes of the prior art to break upon the forceful extrusion/injection of the material.

The kits of the present invention are tailored to adequately and precisely deliver a restorative or injectable composition into an intraosseous space such as a human vertebra when the composition has a very mobile rheology.

In general embodiments of this invention, after the operator creates a space or opening in the bone for the composition, the intraosseous space is augmented with restorative or injectable composition. The augmentation begins with an initial dam being created by a small dosage of composition via the catheter. This dam is created to prevent additional dosages of material from flowing out of the space because of a very mobile rheology. The dam is allowed to cure, the catheter is replaced, and then a second aliquot of the restorative or injectable composition is added to the dam as necessary. This aspect of the invention ensures that all openings are closed with the composition for leakage prevention. Once the second aliquot of composition has cured, additional aliquots of composition can be injected via an additional syringe containing an additional aliquot of material so that the space or opening is completely filled. It is appreciated that additional aliquots will not be necessary for all procedures. Unlike the prior art, an operator using the present invention can routinely set up a dam of material, allow it to harden, and then inject additional doses of material by replacing the catheter. The systems of the present invention uniquely accommodate for mix on demand delivery systems using a delivery gun and mix-tip.

In typical embodiments, the kits of the present invention feature tactile feedback control. When delivering a composition into a vertebra, the cannula 10 is generally inserted substantially close to, but not against, the anterior wall. Some distance is necessary between the cannula 10 and the wall so that the micro-reamer 12 can create a channel. For those embodiments featuring catheters with a side-opening 50, the composition is radially dispersed into the space even if the distal end of the catheter is in contact with the anterior wall. In other embodiments, the syringes of the present invention exemplify the tactile feedback control by allowing the user to apply constant force regardless of volume being inserted. The kit may also include stylets that are sized to fit within the catheter for advancing material through the catheter and clearing any residual material that remains within the catheter.

A number of restorative or injectable compositions can be used within the systems of the present invention. The type of composition used depends upon which procedure is being performed. In some embodiments, the system includes the injection of a plurality of materials including hydrogels, synthetic bone void fillers, polymethylmethacrylate, or replicated bone marrow. In one general embodiment, the system is a syringe filled with material. Specifically, the system is a prefabricated system of material that is directly injected into the syringe or the catheter. In another embodiment, the system for delivery comprises a sole syringe.

Once the channel is created with the micro-reamer 12, the catheter is inserted into the cannula 10 to the same depth previously occupied by the micro-reamer 12. A small amount of restorative or injectable material, between approximately 0.1-1.5 cc, is slowly injected into the catheter, via a syringe filled with restorative or injectable material, under fluoroscopic control while checking for any venous leaks. The catheter can be easily visualized under fluoroscopy either by using a radiopaque material or by adding an agent to the material that makes the material radiopaque. Should a venous leak occur, the injection is immediately stopped, and the catheter removed from the cannula 10 while the cannula remains in place. In this way the access port to the vertebra remains open. After waiting the appropriate amount of time, for example between 2 to 4 minutes, a new catheter is inserted and the injection resumed. Should another venous leak occur, the same procedure is repeated. Once there are no (more) venous leaks, the appropriate volume of material is injected. This technique allows one to make optimal use of a mix-on-demand characteristic of a restorative or injectable material, place the desired amount of material into the site, and eliminate hurrying of the procedure due to concerns of the material setting in the cannula.

Figure 14A:
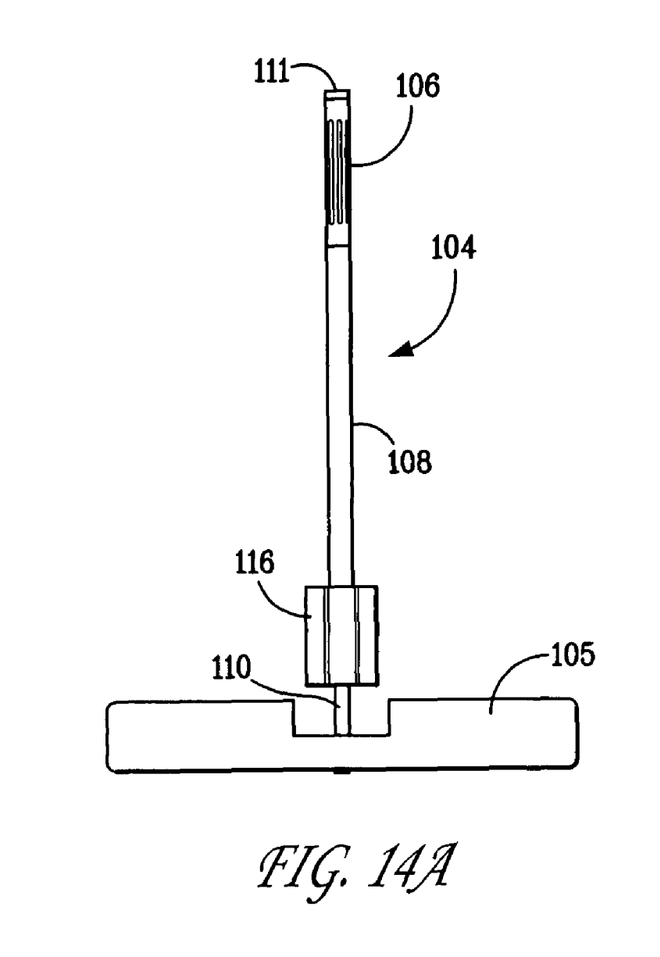
FIG. 14 depicts the expandable micro-reamer with the compression knob.
Figure 14B:
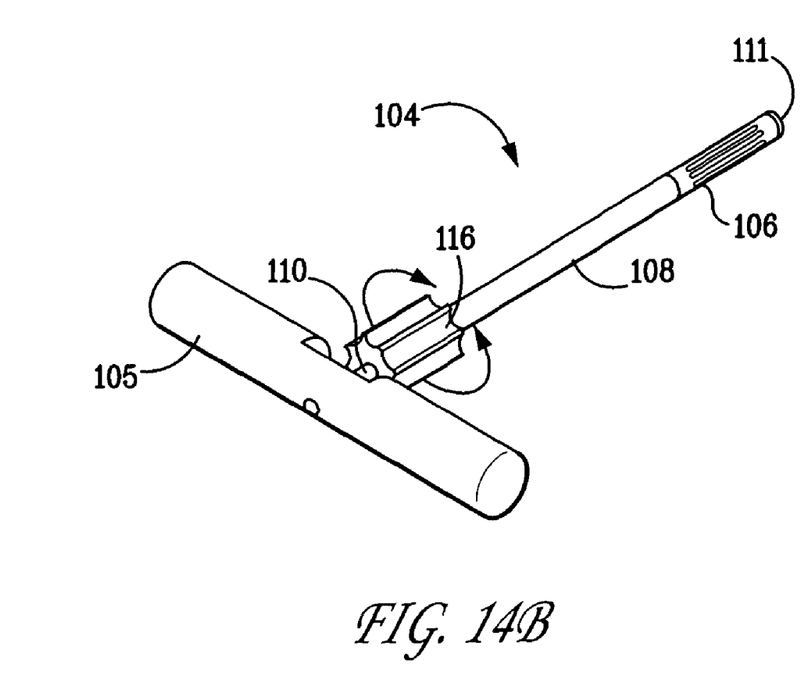

Some embodiments of the present invention may include an expandable micro-reamer 104 (see FIG. 14). This expandable micro-reamer 104 may be used to create or enlarge a space within a vertebral body or other instraossesous space. Such spaces envisioned may be metaphyseal bone areas like distal radius, proximal humerus, proximal femur, distal femur, proximal tibia, distal tibia, calcaneous, or talus.

The expandable micro-reamer 104 comprises an expandable cylindrical section, or bone tamp 106, that is in communication with an outer shaft 108 surrounding an inner shaft 103 of the micro-reamer. The bone tamp 106 has leaves 112 that are formed by slits 114 along the length of the cylindrical section. The leaves 112 flex outwardly, or in the direction opposite of the inner shaft 110, when the bone tamp section 106 is actuated by the outer shaft 108. The bone tamp 106 may be comprised of an elastic metal such as nitinol or other composite/polymer material. As the leaves 112 flex, a space or cavity may be formed through compaction or compression of the surrounding bone or tissue. Restorative or injectable compositions, synthetic bone (allograft or autograft), or cement may be among the compositions injected into the space. The bone tamp 106 may be actuated by turning a compression knob 116 that is in communication with the outer shaft 108. The compression knob 116 may be ribbed or otherwise textured to facilitate turning.

Figure 12A:
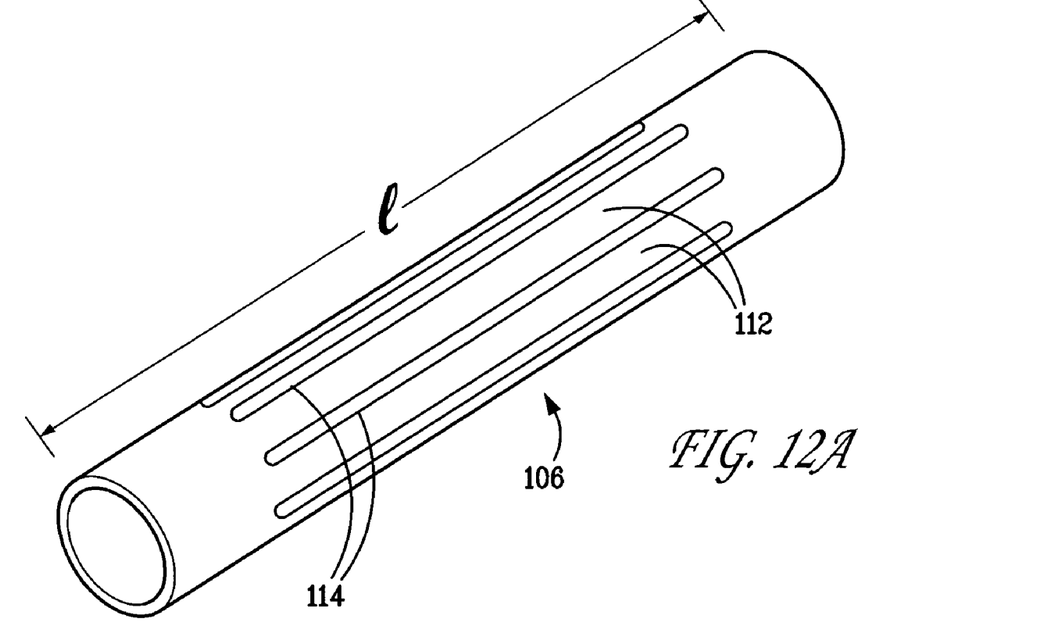
FIG. 12 depicts the cylindrical section of the expandable micro-reamer.
Figure 12B:
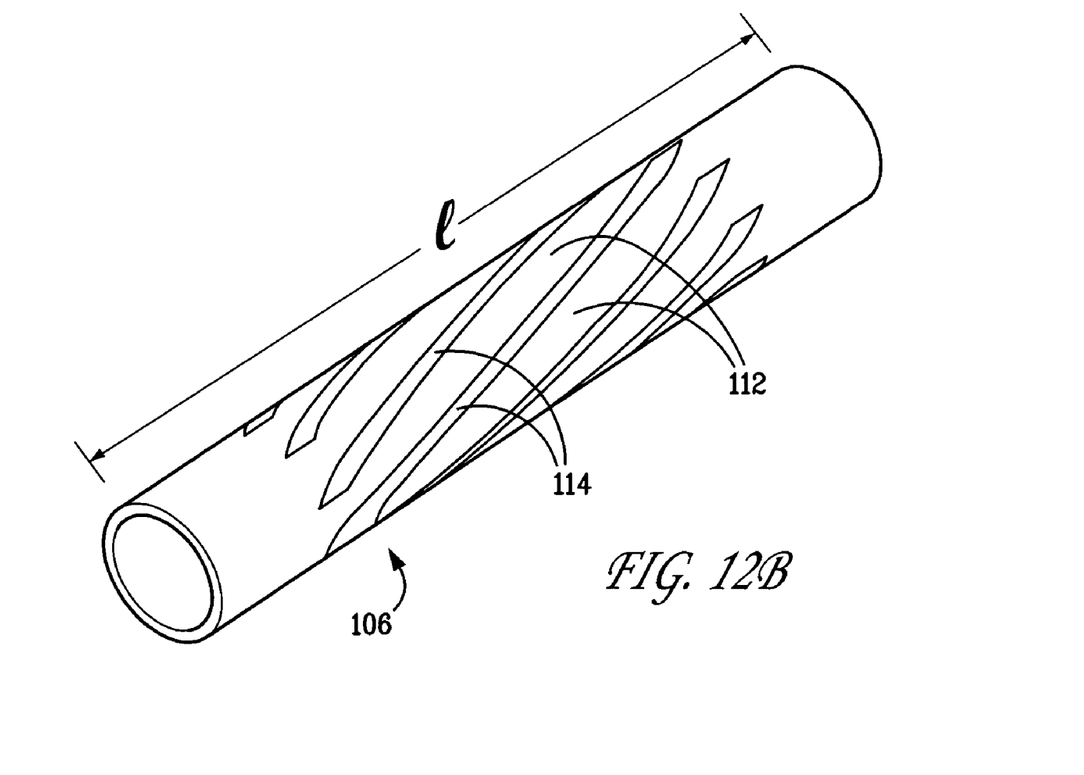

The leaves 112 of the bone tamp 106 may be formed from slits in the cylindrical section along the length of the cylinder as illustrated in FIG. 12. In another embodiment, the leaves 112 of the bone tamp 106 may be formed from slits that are at an angle to the longitudinal axis of the cylinder. As herein defined, the longitudinal axis is an imaginary line that runs centrally along the length of the cylinder from one end to the other. The angle of the slits in relation to the longitudinal axis may be from 5 degrees to 30 degrees, and more preferably from 10 degrees to1 5 degrees. This configuration results in minimal residual deformation, since during expansion, deformation near the middle point of the component is less exaggerated than in the longitudinally-slotted version. This embodiment, where the leaves are at an angle to the length, provides a device that is easily flexed and deformed back to its original shape to present a smooth appearance. In this manner, the micro-reamer can be easily inserted, as well as easily removed from the cannula when desired.

Figure 13A:
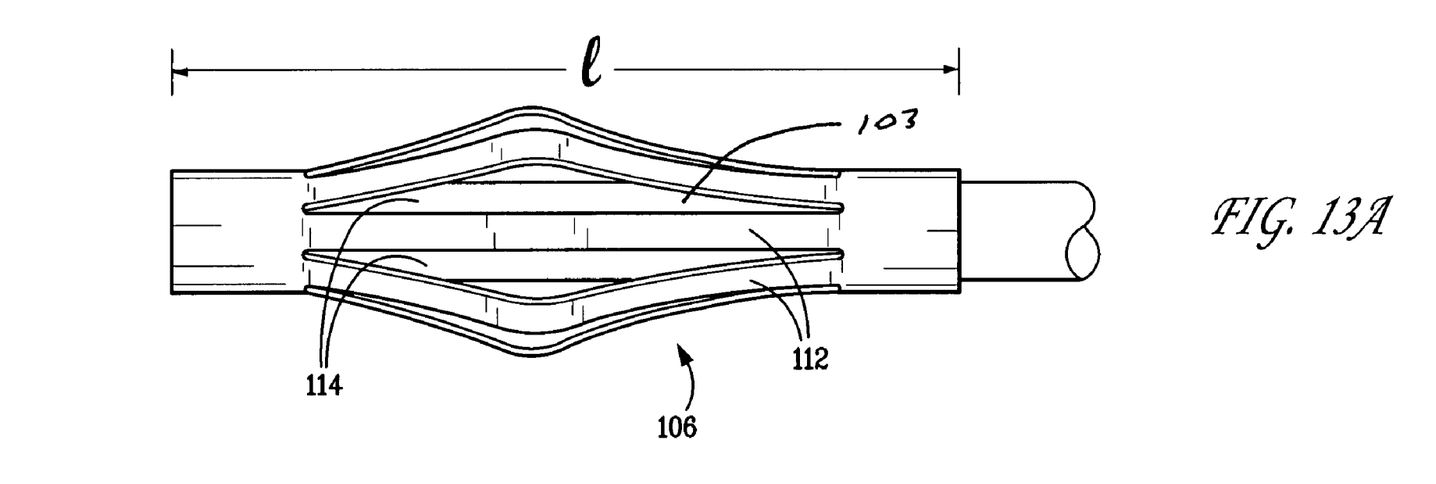
FIG. 13 depicts the expanded leaves of the cylindrical section in parallel and angled formations.
Figure 13B:
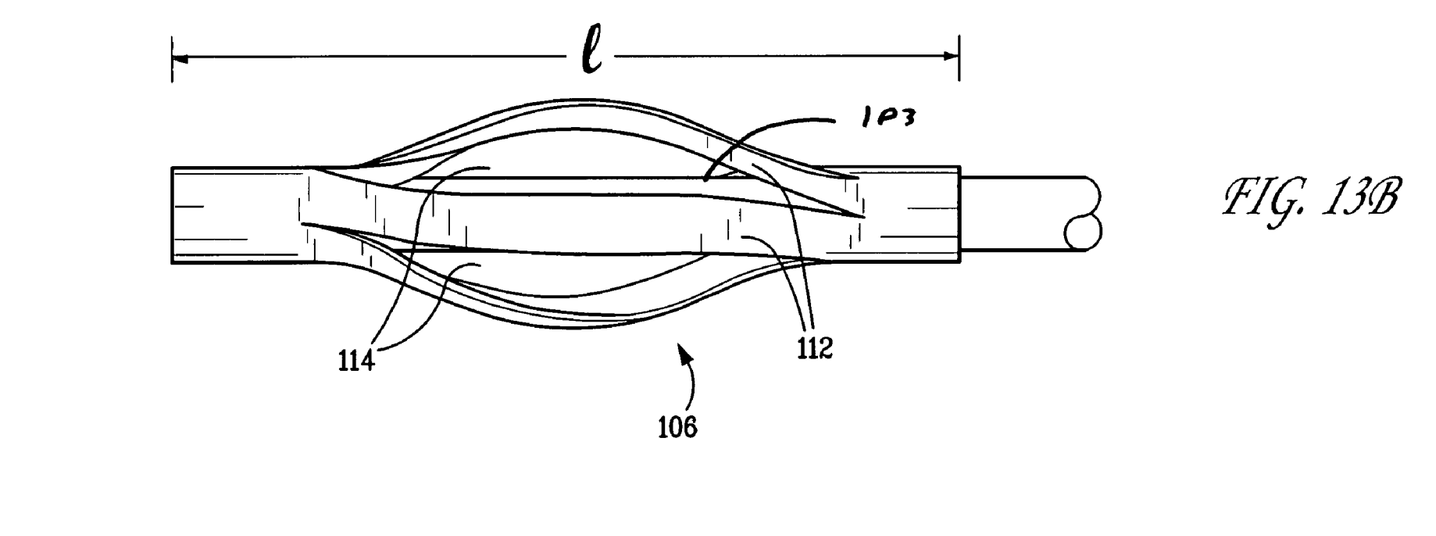

The leaves also expand and form an expansion angle with the cylindrical body when the micro-reamer is actuated. The size of the space created will be directly proportional to the expansion angle in either embodiment. There is a direct relationship between the expansion angle and the space created. This amounts to more compaction of the bone. The expansion angle can vary in size based on desired size of the space to be created and will be affected by the pliability of the material, thickness of the leaves and the like.

An operator may compress bone using the bone tamp or may rotate the tamp to cut bone. The flex, or outward expansion, of the leaves 112 widens the spaces between the leaves 112 and creates an area into which fluids and fat emboli can flow instead of causing these substances to be displaced into the venous blood stream, as occurs with the use kyphoplasty balloons. A space may be formed by flexing the leaves 112 by turning the compression knob 116, then retracting the leaves 112 by rotating the knob 116 in the opposite direction, rotating the bone tamp 106, and then expanding the leaves 112. An operator may cut bone or other tissue by rotating the bone tamp 106 while the leaves 112 are in a partially or fully expanded state. Bone or tissue material that has been freed from the cancellous bone matrix may be subsequently compacted or compressed against the wall of the space by contracting and expanding the bone tamp 106. The size of the space created is dependent upon the pliability of the material and thickness of the leaves, as well as the aspect ratio of the expandable cylindrical section, in an expanded space, and the volume of the expandable cylindrical section, in an expanded state. Once a space has been created or enlarged by the bone tamp, restorative or injectable material may be added. Grading on the cannula 10 that is used to insert the micro reamer 104 may also help the operator in delivering the material.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed:

1. A kit for delivery of a composition into an intraosseous space comprising:
    at least one cannula;
    at least one stylet insertable into the cannula and being movable therein;
    at least one catheter having a substantially rigid high-porosity tip that is insertable into the cannula, wherein said porosity is about 60% to 90%; and
    a system for delivery of aliquots of said composition into the intraosseous space via said catheter;
    wherein said composition comprises a restorative or viscous injectable material.

2. The kit of claim 1 wherein the catheter comprises gradient markings.

3. The kit of claim 1 wherein said high-porosity tip comprises polylactic acid.

4. The kit of claim 1 wherein said high-porosity tip is partially coated with non-porous or semi-porous material that controls the direction of flow of said composition from said high-porosity tip.

5. The kit of claim 4 wherein said material is a ceramic polymer or metal.

6. The kit of claim 4 wherein said material is calcium phosphate, PLLA, or titanium.

7. The kit of claim 4 wherein said material is biocompatible or resorbable.

8. The kit of claim 1 wherein said high porosity tip is biocompatible and resorbable.

9. The kit of claim 1 further comprising a catheter with a plurality of apertures near the distal end.

10. The kit of claim 1 wherein the composition comprises synthetic bone void filler.

11. The kit of claim 1 wherein the composition comprises polymethylmethacrylate.

12. The kit of claim 1 wherein the composition comprises a hydrogel.

13. The kit of claim 1 wherein the composition comprises replicated bone marrow.

14. The kit of claim 1 wherein said high-porosity tip is adapted for being left in or near the intraosseous space following delivery of said composition.

* * * * *